(12) United States Patent
Makarov et al.

(10) Patent No.: US 8,962,634 B2
(45) Date of Patent: Feb. 24, 2015

(54) 4-AMINO-3-ARYLAMINO-6-ARYLPYRAZOLO[3,4-D) PYRIMIDINE DERIVATIVES, METHODS FOR THEIR PREPARATION AND THEIR USE AS ANTIVIRAL AGENTS

(75) Inventors: Vadim Albertovitch Makarov, Moscow (RU); Peter Wutzler, Erfurt-Windischholzhausen (DE); Michaela Schmidtke, Jena (DE); Hans-Martin Dahse, Jena (DE)

(73) Assignee: Dritte Patentportfolio Beteiligungsgesellschaft mbH & Co. KG, Schoenefeld, OT Waltersdorf (DE)

( * ) Notice: Subject to any disclaimer, the term of this patent is extended or adjusted under 35 U.S.C. 154(b) by 840 days.

(21) Appl. No.: 12/308,729

(22) PCT Filed: Jun. 20, 2007

(86) PCT No.: PCT/DE2007/001104
§ 371 (c)(1),
(2), (4) Date: Apr. 24, 2009

(87) PCT Pub. No.: WO2007/147401
PCT Pub. Date: Dec. 27, 2007

(65) Prior Publication Data
US 2010/0010018 A1    Jan. 14, 2010

(30) Foreign Application Priority Data
Jun. 22, 2006 (DE) .......................... 10 2006 029 074

(51) Int. Cl.
*A61K 31/519*  (2006.01)
*C07D 487/00*  (2006.01)
*C07D 487/04*  (2006.01)

(52) U.S. Cl.
CPC .................................. *C07D 487/04* (2013.01)
USPC ....................................... 514/262.1; 544/262

(58) Field of Classification Search
CPC ........................... C07D 487/22; A61K 31/519
USPC ....................................... 514/262.1; 544/262
See application file for complete search history.

(56) References Cited

U.S. PATENT DOCUMENTS

| 2,965,643 | A | 12/1960 | Riehen et al. |
| 3,600,389 | A | 8/1971  | Riehen et al. |
| 4,904,666 | A | 2/1990  | Friebe et al. |
| 5,294,612 | A | 3/1994  | Bacon et al.  |

FOREIGN PATENT DOCUMENTS

| DE | 1 088 503 | 9/1960 |
| EP | 0 496 617 | 7/1992 |
| EP | 0 674 642 | 8/2000 |
| EP | 0 691 128 | 12/2002 |
| WO | WO-00/43394 | 7/2000 |
| WO | WO-2006/035061 | 4/2006 |

OTHER PUBLICATIONS

Harley A. Rotbart, "Treatement of picornavirus infections", Antiviral Research 53 (2002), pp. 83-98.
S. Crotty, et al., "The broad-spectrum antiviral ribonucleoside ribavirin is an RNA virus mutagen", Nature Medicine, vol. 6, No. 12, Dec. 2000, pp. 1375-1379.
B. A. Heinz, et al., "The Antiviral Compound Enviroxime Targets the 3A Coding Region of Rhinovirus and Poliovirus", Journal of Virology, Jul. 1995, vol. 69, No. 7, pp. 4189-4197.
F. D. Miller, et al., "Controlled Trial of Enviroxime Against Natural Rhinovirus Infections in a Community", Antimicrobial Agents and Chemotherapy, Jan. 1985, vol. 27, No. 1, pp. 102-106.
A, K. Patick, et al., "In Vitro Antiviral Activity of AG 7088, a Potent Inhibitor of Human Rhinovirus 3C Protease", Antimicrobial Agents and Chemotherapy, Oct. 1999, vol. 43, No. 10, pp. 2444-2450.
G. D. Diana, "Inhibitors of Picornavirus Replication", Curr. Med. Chem., 2003, 2, pp. 1-12.
D. C. Pevear, et al., "Activity of Pleconaril against Enteroviruses", Antimicrobial Agents and Chemotherapy, Sep. 1999, vol. 43, No. 9, pp. 2109-2115.
M. A. McKinlay, et al., "Treatment of the Picornavirus Common Cold by Inhibitors of Viral Uncoating and Attachment", Annual Reviews Microbiol, 1992, 46, pp. 635-654.
R. M. Ledford, et al., "VPI Sequencing of All Human Rhinovirus Serotypes: Insights into Genus Phylogeny and Susceptibility to Antiviral Capsid-Binding Compounds", Journal of Virology, Apr. 2004, vol. 78, No. 7, pp. 3663-3674.
J. M. Groarke, et al., "Attenuated Virulence of Pleconaril-Resistant Coxsackievirus B3 Variants", The Journal of Infectious Diseases, 1999, 179(6), 1538-1541.
M. J. Abzug, et al., "Double blind placebo-controlled trial of pleconaril in infants with enterovirus meningitis", The Pediatric Infectious Disease, 2003, 22, pp. 335-341.
F. G. Hayden, et al., "Oral pleconaril treatment of picornavirus-associated viral respiratory illness in adults: efficacy and tolerability in Phase II clinical trials", Antiviral Therapy, 2002, 7, pp. 53-65.

(Continued)

*Primary Examiner* — Shengjun Wang
(74) *Attorney, Agent, or Firm* — Jordan and Hamburg LLP

(57) ABSTRACT

4-amino-3-arylamino-6-arylpyrazolo[3,4-d]pyrimidine derivatives of general formula (I), pharmaceutically acceptable salts thereof, method for preparation of the aforesaid compounds and their use as antiviral agents.

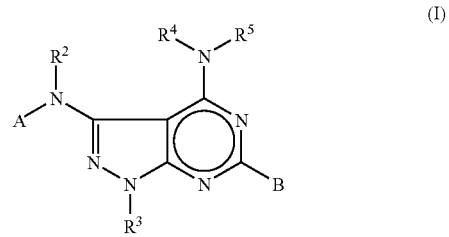

(I)

10 Claims, No Drawings

(56) References Cited

OTHER PUBLICATIONS

F. G. Hayden, et al., "Efficacy and Safety of Oral Pleconaril for Treatment of Colds Due to Picornaviruses in Adults: Results of 2 Double-Blind, Randomized, Placebo-Controlled Trials", Clinical Infectious Diseases, 2003, 36, pp. 1523-1532.

K. Senga, et al., "Synthesis and Xanthine Oxidase Inhibitory Activity of 4,6-Disubstituted 1-*p*-Chlorophenylpyrazolo[3,4-*d*]pyrimidines", Chem., Nov.-Dec. 1982 vol. 19, pp. 1565-1567.

Y. Tomiga, et al., "Sythesis of Pyrazolo[3,4-*d*]pyrimidine Derivatives Using Ketene Dithioacetals", Chem., Mar.-Apr. 1990, 27, pp. 775-779.

R. T. Boere, et al., "Preparation of *N,N,N'*-tris(trimethylsilyl)amidines; a convenient route to unsubstituted amidines", Journal of Organometallic Chemistry, 331 (1987), pp. 161-167.

R. S. Garigipati, "An Efficient Conversion of Nitriles to Amidines", Tetrahedron Letter, 1990, vol. 31, No. 14, pp. 1969-1972.

O. Dann, et al., "Synthesen biskationischer, trypanocider 1-Benzofuran-Verbindungen", Justus Liebigs Ann. Chem., 1982, pp. 1836-1869.

D. Briel, et al.; "Synthese substituierter 6-Phenylpyrazolo[3,4-*d*]pyrimidine mit potenziell Adenosin-$A_{2A}$-antagonistischer Wirkung"; Parmazie 60, (2005), pp. 732-733.

Howard B. Cottam, et al.; Synthesis and Biological Acitivity of Certain 3, 4-Disubstituted Pyrazolo[3, 4-*d*]pyrimidine Nucleosides1; American Chemical Society (1984) 2 Pages.

4-AMINO-3-ARYLAMINO-6-ARYLPYRAZOLO [3,4-D) PYRIMIDINE DERIVATIVES, METHODS FOR THEIR PREPARATION AND THEIR USE AS ANTIVIRAL AGENTS

BACKGROUND OF THE INVENTION

The invention relates to 4-amino-3-arylamino-6-arylpyrazolo[3.4-d]-pyrimidine derivatives, methods for their preparation and their use as antiviral agents, preferably for the treatment of picornavirus infections.

Picornaviruses, particularly entero- and rhinoviruses, are responsible for a broad spectrum of human diseases. More than 60 different human pathogenic serotypes belong to the enteroviruses (Melnick J in: Fields B et al., editors. Virology. Philadelphia: Lippincott-Raven Publishers; 1996, 655-712). Enterovirus, echovirus, coxsackievirus A and B infections are often characterized by nonspecific fever and cause diseases of the upper respiratory system that often cannot be distinguished from rhinovirus infections. The more serious clinical pictures, which can also occur epidemically, comprise hemorrhagic conjunctivitis, herpangina, hand-foot-and-mouth-disease, aseptic meningitis, encephalitis and acute myocarditis. The problem here is that different types of viruses can cause the same symptoms or one virus type can cause totally different clinical pictures. Thanks to the introduction of modern and sensitive methods in virus diagnostics persistent enteroviral RNA and virus proteins could be identified in connection with chronic diseases such as type II diabetes, poliomyositis and most of all chronic myocarditis. Persistent enterovirus infections also occur in patients with agammaglobulinemia and manifest themselves here as persistent enterovirus meningoencephalitis. Dermatomyositis or polymyositis often appeared as accessory symptoms. The rhinoviruses comprise about 100 serotypes. Rhinovirus infections cause more than half of all respiratory diseases of the upper respiratory system in humans (Couch R B in: Fields B M et al., editors: Fields Virology, 3$^{rd}$ edition. Lippincott-Raven, Philadelphia, 1996, 713-35). For a mean period of illness of about 10 days these colds that take mostly a harmless course cause million fold visits to a doctor's and losses of working and school hours. Possible complications that can occur are otitis media, sinusitis, exacerbation of asthma and cystic fibrosis as well as infections of the lower respiratory system mostly in small children, elderly patients and immunosuppressed patients. As a great variety of types exists, a vaccination prophylaxis is not possible at present. Due to the losses of working hours, visits to a doctor's and medicaments combined with these diseases, rhino- and enteroviruses cause enormous expenses every year. Theses virus infections have been treated symptomatically up to now because virus-specific therapeutics are not available (Rotbart H A: *Antiviral Res* 2002, 53(2), 83-98). Moreover, antibiotics are often prescribed unnecessarily. Therefore, the development of new virostatics is essential.

The results of the intensive search for possible treatments of enterovirus and rhinovirus infections were summarized by Rotbart in 2002 in a general review article (Rotbart H A: *Antiviral Res* 2002, 53(2), 83-98). For example, ribavirin inhibits a host cell enzyme, the inosin 5'-monophosphate (IMP)-dehydrogenase. By deactivating this key enzyme for the synthesis of purinnucleotides the replication of picornaviruses can be inhibited in vitro and in vivo. Moreover, ribavirin shall be directly built into the genome of polioviruses and thus additionally act as a mutagen for RNA viruses (Crotty S et al.: *Nat Med*, 2000, 6(12),1375-9). Due to the serious side effects these compounds are not used for treating infections caused by rhino- and enteroviruses.

Specific targets for the inhibition of the viral RNA synthesis are the genome itself, the viral RNA-dependent RNA polymerase and further viral proteins required for the replication complex. For a long time, guanidines, thiosemicarbazones, benzimidazoles, dipyridamoles and flavones have been known as inhibitors of the polymerases of different picornaviruses in the cell culture. Varying degrees of success could be achieved in vivo in this way. Enviroxime derivatives are considered the most promising candidate with a broad anti-enterovirus- and anti-rhinovirus activity. Enviroxime impedes the synthesis of plus-strand RNA by the binding to the virus protein 3A that is required for the formation of RNA intermediates in the virus reproduction (Heinz B A and Vance L M: *J Virol,* 1995, 69(7), 4189-97). Moderate or no therapeutic effects, a bad pharmacokinetics and unwanted side effects were observed in clinical studies (Miller F D et al.: *Antimicrob Agents Chemother,* 1985, 27(1), 102-6). Up to now, clinical data of newer derivatives with better bioavailability and tolerance do not exist.

The protease inhibitor AG 7088 has been developed on the basis of the knowledge about the fine structure and function of the viral protease 2C. In the cell culture in the nanomolar concentration range, AG 7088 has an effect against 48 rhinovirus types and coxsackievirus A21, B3, enterovirus 70 and echovirus 11 (Pattick A K et al.: *Antimicrobila Agents Chemother,* 1999, 43(10), 2444-50). The final data of the clinical studies are not known so far.

Thanks to the clarification of the molecular structure of the viral capsids, the preconditions for a purposeful design of capsid blockers, the "WIN substances", have been obtained (Diana G D: *Curr Med Chem* 2003, 2, 1-12). They inhibit the adsorption and/or the uncoating of rhino- and enteroviruses. Some of the WIN substances have a highly specific effect only against individual genera or virus types of the picornaviruses. Other derivatives inhibit the replication both of rhino- and enteroviruses. Arildone, disoxaril and pirodavir belong for example to the WIN substances. These compounds showed very good antiviral effects in the cell culture. A poor solubility (arildone), low bioavailability (arildone and disoxaril), a rapid metabolization and excretion (disoxaril and WIN 54954) as well as side effects, such as skin rash (WIN 54954), made a clinical application impossible. Great hopes were placed in pleconaril, a further capsid inhibitor. Pleconaril has a very good oral bioavailability and after its binding to the hydrophobe pocket in the viruscapsid it inhibits the penetration of rhino-, echo- and coxsackviruses (Pevear D C et al.: *Antimicrob Agents Chemother* 1999, 43(9), 2109-15; McKinlay M A et al.: *Annu Rev Microbiol* 1992, 46, 635-54). Therefore, it is potentially effective against a broad spectrum of virus diseases, from the common cold to the viral meningitis or myocarditis. Resistances were observed for rhinoviruses, enterovirus 71 and coxsackievirus B3 (Ledford R M et al.: *J Virol* 2004, 78(7), 3663-74; Groarke J M et al.: *J Infect Dis* 1999, 179(6), 1538-41). Clinical studies in children and adults with an enterovirus meningitis (Abzug M J et al.: *Pediatr Infect Dis J,* 2003, 22, 335-41) and respiratory infections caused by rhinovirus (Hayden F G et al.: *Antivir Ther,* 2002, 7, 53-65; Hayden F G et al.: *Clin Infect Dis,* 2003, 36, 1523-32) took a positive course. However, the proven therapeutic effect was not sufficient for the registration of pleconaril (Picovir, Viropharma, USA) as an agent for the treatment of rhinovirus infections in the USA. In March 2002, a corresponding application was refused by the Food and Drug Administration (FDA) because of a too low therapy success with simultaneously observed side effects.

Pyrazolopyrimidines have also been described as CRF antagonists (e.g. EP 674 642 and EP 691 128) that for example inhibit the adenosine kinase (EP 496 617 or U.S. Pat. No. 4,904,666), the xanthine oxigenase (J. Heterocyc. Chem. 19, 1565, 1982) or other enzyme systems (U.S. Pat. Nos. 2,965,643 and 3,600,389).

Thus, the development of highly effective virustatics for the treatment of rhino- and enterovirus diseases continues to be an essential task in antiviral research. The novel compounds should be well tolerated and get over existing resistances, e.g. against pleconaril.

SUMMARY OF THE INVENTION

The aim of this invention is to provide novel compounds that can be employed as antivirus agents against enteroviruses and rhinoviruses and avoid the explained disadvantages of the state of the art, particularly the problems concerning the resistance and intolerance against the corresponding medicaments, as well as to describe the preparation and use of said compounds.

According to the invention, this task is fulfilled by specifically substituted 4-amino-3-arylamino-6-arylpyrazolo[3,4-d]pyrimidine derivatives of the general formula I, their pharmaceutically tolerated salt compounds included,

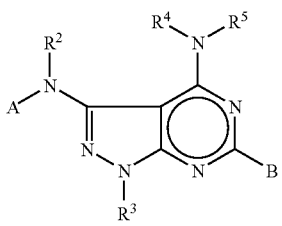

(I)

wherein:
the groups A and B are, independently of each other, phenyl, naphthyl, pyridyl, chinolyl, pyrazinyl, pyrimidyl, pyrazolyl, triazinyl, imidazolyl, furanyl, thienyl and in each of the just mentioned groups, independently of each other, one to three hydrogen atoms can be substituted by a $R^1$ group specified in the following,
the $R^1$ group can be $NO_2$, CN, $CONR^2_2$, $COOR^2$, CHO, $CONH_2$ a halogen, a saturated or unsaturated, linear or branched aliphatic radical with 1-7 chain components, a saturated or unsaturated, linear or branched alkanol radical with 1-8 chain components, $OR^2$, $SR^2$, $NR^2_2$, $SO_2NR^3_2$, di- or trifluoromethyl, phenyl,
the $R^2$, $R^3$, $R^4$, $R^5$ groups are, independently of each other, H, a saturated or unsaturated, halogenated or non-halogenated, linear or branched aliphatic radical with 1-7 chain components, benzyl, phenyl or naphtyl, in a saturated or unsaturated, mono- or polyheterocycle with the heteroatoms N, S, O and each of the just mentioned groups can be substituted independently with fluorine, chlorine, bromine, trifluormethyl, alkyl, alkoxy, cyano, nitro, amino, aminoalkyl, C(O)-alkyl, C(O)O-alkyl, benzyl, phenyl or naphtyl.

Preferred compounds of the invention include 4-amino-6-phenyl-3-(tri-R1)phenylaminopyrazolo[3,4-d]pyrimidine and 1-R3-4-amino-6-phenyl-3-(tri-R1)phenylaminopyrazolo[3,4-d]pyrimidine of the general formula (I) wherein the group R1 in the groups A and B are, independently of each other, CONH2, CN, halogen, NO2, or CF3. Preferred compounds of the invention also include 6-phenylaminopyrazolo [3,4-d]pyrimidines of the general formula (I) wherein the group R1 in the groups A and B are, independently of each other, a halogen.

In a preferred embodiment the invention relates to compounds of the general formula (I), selected from the group of 6-phenylaminopyrazolo[3,4-d]pyrimidines comprising:
4-amino-6-phenyl-3-(tri-$R^1$)phenylaminopyrazolo[3,4-d]pyrimidine,
4-amino-6-(tri-$R^1$)phenyl-3-phenylaminopyrazolo[3,4-d]pyrimidine,
1-alkyl-4-amino-6-phenyl-3-(tri-$R^1$)phenylaminopyrazolo[3,4-d]pyrimidine,
4-amino-1,6-di(tri-$R^1$)phenyl-3-phenylaminopyrazolo[3,4-d]pyrimidine,
4-amino-6-phenyl-3-(tri-$R^1$)phenylalkylaminopyrazolo[3,4-d]pyrimidine,
1-alkyl-4-amino-6-phenyl-3-(tri-$R^1$)phenylalkylaminopyrazolo[3,4-d]pyrimidine.

Advantageously, the invention also includes 6-phenylamino-pyrazolo[3,4-d]pyrimidines of the general formula (I) comprising:
4-amino-3-(3-fluorophenyl)amino-6-phenylpyrazolo[3,4-d]pyrimidine,
4-amino-3-(3-fluorophenyl)amino-6-(4-chlorophenyl)pyrazolo[3,4-d]pyrimidine,
4-amino-3-(3-chloro)amino-6-phenylpyrazolo[3,4-d]pyrimidine,
4-amino-3-(3-methoxy)amino-6-phenylpyrazolo[3,4-d]pyrimidine,
4-amino-3-(4-fluorophenyl)amino-6-phenylpyrazolo[3,4-d]pyrimidine,
4-amino-3-(4-fluorophenyl)amino-6-(4-chlorophenyl)pyrazolo[3,4-d]pyrimidine,
4-amino-3-(4-chlorophenyl)amino-6-phenylpyrazolo[3,4-d]pyrimidine,
4-amino-3-(3-fluorophenyl)amino-1-methyl-6-phenylpyrazolo[3,4-d]pyrimidine,
4-amino-1-benzyl-3-(3-fluorophenyl)amino-6-phenylpyrazolo[3,4-d]pyrimidine.

Surprisingly, the compounds of this invention show a strong antiviral activity against picornaviruses, particularly against entero- and rhinoviruses in the nano- or micromolar concentration range.

Therefore, the inventive pharmaceutical preparations that contain a compound of formula (I) are particularly suitable for the treatment of respiratory infections, of aseptic meningitis, encephalitis, herpangina etc. in humans and animals that can be caused by picornaviruses, entero- and rhinoviruses in particular.

In the following, the invention is explained in detail by means of synthesis processes, special 4-amino-3-arylamino-6-arylpyrazolo[3,4-d]pyrimidine derivatives of the general formula (I) as well as their effect and use against picornavirus infections.

FIG. 1 shows a general scheme for the synthesis of the inventive pyrazolo[3,4-d]pyrimidine 1 and in the first step it includes the condensation of [bis(methylthio)methylen]malononitril 2 with arylamines 3 in alcohol to aryl derivatives 4. Each of the latter can be isolated and purified for further reactions or be used directly for subsequent reactions without purification (one-pot reaction). The next step is the interaction of the aryl derivative 4 with hydrazine or hydrazine derivatives. The reaction goes on under boiling during 1 through 4 hours and leads to a high yield of pyrazol 5. The decisive step of the synthesis of pyrazolo[3,4-d]pyrimidine 1 is the condensation of pyrazol 5 with arylamidines 6 in the presence of ethanoic acid, trifluor ethanoic acid or sodium acetate.

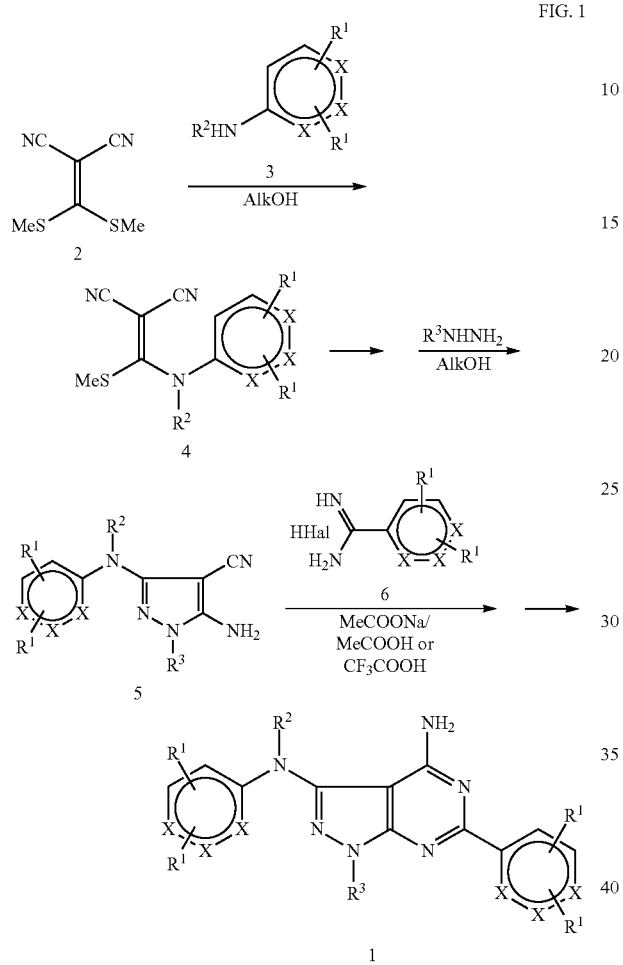

FIG. 1

An alternative synthesis method is the one-pot reaction of malononitril with arylisothiocyanates in the presence of sodium hydride and the subsequent treatment of the reaction mixture with iodinmethyl or dimethylsulphate. In this process, large quantities of enamines are produced. The condensation of pyrazol 5 with arylamidines 6 in the presence of acid, such as ethanoic acid, trifluor ethanoic acid or their salts (acetate) is the decisive synthesis step also here for the production of pyrazolo[3,4-d]pyrimidine 1.

The following examples list the special compounds of the general formula (I) that are preferably used for applications against picornavirus infections (without restricting the invention to them), and the inventive compounds can be prepared in a solution or a suspension in a pharmaceutically acceptable aqueous, organic or aqueous-organic medium for the local or parental application by intravenous, subcutaneous or intramuscular injection or for the intranasal administration, or they are formed as a pill, capsule or aqueous suppository.

The presented compounds of formula (I) can be used in doses ranging from 0.1 to 1000 mg/kg of the body weight.
1. Preparation and Analysis of the 4-amino-3-arylamino-6-arylpyrazolo[3,4-d]pyrimidine derivatives The structure of the inventive compounds was clarified by the kind of synthesis, elementary analyses, NMR spectroscopy and mass spectroscopy.
Source Materials:
The 5-amino-4-cyano-3-arylaminopyrazoles have been synthesized according to the procedure shown in FIG. 1 and the description of Tominaga Y et al. (*J. Heterocycl. Chem.,* 1990, 27, 775-779). According to the state of the art, arylamidines have been synthesized from the corresponding cyanogen source compounds (Boere, R T et al.: *J. Organomet. Chem.,* 1987, 331, 161-167; Garigipati R S: *Tetrahedron Lett.,* 1990, 31, 1969-1978; Dann O et al.: *Justus Liebigs Ann. Chem.,* 1982, 1836-1839).

EXAMPLE 1

4-amino-3-phenylamino-6-phenylpyrazolo[3,4-d]pyrimidine 3.0 g (17.24 mmol) benzamidin hydrochloride hydrate and 2.2 g (23.0 mmol) sodium acetate are added to 2.3 g (11.5 mmol) 5-amino-4-cyano-3-phenylaminopyrazol by stirring. The reaction mixture is heated at 220° C. for 30 minutes. The obtained material is treated with 50 ml water, filtered and washed with 20 ml of cold methanol and 20 ml of cold ester. The product is purified by means of crystallization from DMF/water.
Light-yellow, solid crystalline substance. Yield 57%. mp 253-5° C.
$R_f$(chloroform-methanol; 10/1)-0.8 (silica gel 60).
MS m/z 302 (M$^+$).

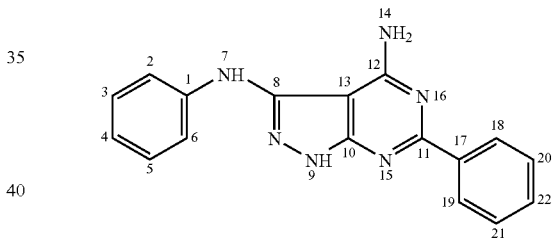

$^1$H NMR (DMSO-d$_6$) δ 12.38 (1H, s, NH(9)), 8.32-8.36 (2H, q, CH(18), CH(19)), 8.23 (1H, br. s, NH(7)), 7.67 (2H, d, CH(2), CH(6)), 7.48 (2H, br. s, NH$_2$), 7.42 (3H, m, CH(20), CH(21), CH(22)), 7.12 (2H, d, CH(3), CH(5)) and 6.98 (1H, m, CH(4)) ppm.
$^{13}$C NMR (DMSO-d$_6$) δ 161.0 (C(11)), 156.2 (C(12)), 153.0 (C(10)), 144.2 (C(8)), 138.3 (C(17)), 136.0 (C(1)), 130.3 (C(4)), 129.8 (C(22)), 128.8 (C(3), C(5)), 128.0 and 127.7 (C(18), C(19)), 120.4 (C(4)), 120.2 (C(2), C(6)), 88.7 (C(13)) ppm.
Calculated for C$_{17}$H$_{14}$N$_6$: C, 67.54; H, 4.67; N, 27.80
Found: C, 67.61; H, 4.82; N, 27.79

EXAMPLE 2

4-amino-3-(3-fluorophenyl)amino-6-phenylpyrazolo[3,4-d]pyrimidine

The preparation follows the method described in example 1.
Light-yellow, solid crystalline substance. Yield 46%. mp 267-9° C.
$R_f$(chloroform-methanol; 10/1)-0.85 (silica gel 60)
MS m/z 320 (M$^+$). .

¹H NMR (DMSO-d₆) δ 12.61 (1H, s, NH(9)), 8.35-8.38 (2H, q, CH(18), CH(19)), 8.64 (1H, br. s, NH(7)), 7.46 (2H, br. s, NH₂), 7.3-7.52 (6H, m, CH(2), CH(4), CH(6), CH(20), CH(21), CH(22)), 6.60 (1H, t, CH(5)) ppm.

¹³C NMR (DMSO-d₆) δ 166.2 and 161.2 (C(3)), 162.2 (C(11)), 161.8 (C(10)), 156.1 (C(12)), 144.3 (C(1)), 143.4 (C(8)), 130.0 (C(17)), 129.8 (C(5)), 128.5 (C(22)), 127.0 (C(18), C(19)), 112.5 (C(6)), 105.5 and 105.8 (C(2)), 102.6 and 103.9 (C(4)), 89.39 (C(13)) ppm.

Calculated for C17H14 F N6: C, 63.74; H,4.09; N, 26.24
Found: C, 63.60; H, 4.02; N, 27.99

EXAMPLE 3

4-amino-3-(3-methylphenyl)amino-6-phenylpyrazolo[3,4-d]pyrimidine

The preparation follows the method described in example 1.

Almost white, solid crystalline substance. Yield 73%. mp 246-8° C.

$R_f$(chloroform-methanol; 10/1)-0.90 (silica gel 60).
MS m/z 316 (M⁺).

¹H NMR (DMSO-d₆) δ 12.38 (1H, s, NH(9)), 8.32-8.36 (2H, q, CH(18), CH(19)), 8.23 (1H, br. s, NH(7)), 7.42-7.67 (6H, m, NH₂, CH(6), CH(20), CH(21), CH(22)), 7.21-7.29 (2H, m, CH(2), CH(5)) and 6.42 (1H, d, CH(4)), 2.17 (3H, s, CH₃) ppm.

Calculated for $C_{18}H_{16}N_6$: C, 68.34; H, 5.10; N, 26.56
Found: C, 68.43; H, 5.16; N, 26.71

EXAMPLE 4

4-amino-3-(4-methylphenyl)amino-6-phenylpyrazolo[3,4-d]pyrimidine

The preparation follows the method described in example 1

The physico-chemical parameters are the following ones:
Almost white, solid crystalline substance. Yield 43%. mp 266-8° C.

$R_f$(chloroform-methanol; 10/1)-0.85 (silica gel 60).
MS m/z 316 (M⁺).

¹H NMR (DMSO-d₆) δ 12.38 (1H, s, NH(9)), 8.33-8.38 (2H, q, CH(18), CH(19)), 8.15 (1H, br. s, NH(7)), 7.60 (2H, d, CH(2), CH(6)), 7.48 (2H, br. s, NH₂), 7.42 (3H, m, CH(20), CH(21), CH(22)), 6.84 (2H, d, CH(3), CH(5)) and 2.34 (3H, s, CH₃) ppm.

¹³C NMR (DMSO-d₆) δ 161.0 (C(11)), 156.2 (C(12)), 153.0 (C(10)), 144.2 (C(8)), 138.3 (C(17)), 136.0 (C(1)), 130.3 (C(4)), 129.8 (C(22)), 128.0 and 127.7 (C(18), C(19)), 123.8 (C(3), C(5)), 118.2 (C(2), C(6)), 88.9(C(13)), 20.8 (CH₃) ppm.

Calculated for $C_{18}H_{16}N_6$: C, 68.34; H, 5.10; N, 26.56
Found: C, 68.38; H, 5.07; N, 26.47

EXAMPLE 5

4-amino-3-(4-bromophenyl)amino-6-phenylpyrazolo [3,4-d]pyrimidine 1.87 g (10.7 mmol) benzamidin hydrochloride hydrate and 0.89 g (10.7 mmol) sodium acetate are added to 1.0 g (3.6 mmol) 5-amino-4-cyano-3-(4-bromophenyl)aminopyrazol in 20 ml ethanoic acid by stirring. The reaction mixture is boiled for a period of 4 h, treated with 50 ml water, filtered and washed with 20 ml of cold methanol and 20 ml of cold ester. The raw product is purified by means of crystallization from ethanol.

The physico-chemical parameters are the following ones:
Yellow, crystalline, solid substance. Yield 38%. mp 272-4° C.

$R_f$(chloroform-methanol; 10/1)-0.9 (silica gel 60).
MS m/z 381 (M⁺).

¹H NMR (DMSO-d₆) δ 12.44 (1H, s, NH(9)), 8.33-8.38 (2H, q, CH(18), CH(19)), 8.12 (1H, br. s, NH(7)), 7.40-7.53 (7H, m, NH₂, CH(3), CH(5), CH(20), CH(21), CH(22)), 7.10 (2H, d, CH(2), CH(6)) ppm.

Calculated for $C_{17}H_{13}BrN_6$: C, 53.65; H, 3.44; N, 22.04
Found: C, 5.80; H, 3.48; N, 21.95

EXAMPLE 6

4-amino-3-(4-fluorophenyl)amino-6-phenylpyrazolo [3,4-d]pyrimidine

The synthesis follows the method described in example 5, trifluor ethanoic acid is used as a solvent. The crystallization of the end product is made from ethanol/DMF.

The physico-chemical parameters are the following ones:
White-yellow, crystalline, solid substance. Yield 58%. mp 259-263° C.

$R_f$(chloroform-methanol; 10/1)-0.8 (silica gel 60).
MS m/z 320 (M⁺).

¹H NδMR (DMSO-d₆) δ 12.69 (1H, s, NH(9)), 8.33-8.41 (4H, m, CH(2), CH(6),CH(18), CH(19)), 8.18 (1H, br. s, NH(7)), 7.58-65 (5H, m, NH₂, CH(20), CH(21), CH(22)), 7.27-7.31 (2H, m, CH(3), CH(5)) ppm.

Calculated for $C_{17}H_{14}F\ N_6$: C, 63.74; H, 4.09; N, 26.24
Found: C, 63.57; H, 4.07; N, 26.33

2. Use of the Inventive 4-amino-3-arylamino-6-arylpyrazolo [3,4-d]pyrimidine Derivatives as Antiviral Agents 2.1 Tolerance of the Compounds of the Just Described Examples 1 through 6 in the Cell Culture:

1×10⁴ HeLa cells (DSMZ, ACC 57) were seeded per microtestplate cavity in 0.2 ml culture medium RPMI 1640. The microtiter plates were incubated without the test substance according to standard (at 37° C., 5% $CO_2$ and ca. 95% relative humidity) for 48 hours under physiological conditions to produce subconfluent monolayers. Afterwards, dilution stages of the test substances were added to the monolayers and incubated under physiological conditions during a period of 72 h. At the end of the time of incubation, the extinction of all cavities of the microtiterplates were measured at 660 nm by means of a microplate reader (Sunrise, TECAN) after glutaraldehyd fixation and methylen-blue dye and the $CC_{50}$ was determined by the analysis program "Magellan". As the pre-incubation of the HeLa cells already leads to the formation of a subconfluent cell lawn, the cytolysis during the subsequent incubation with the test substance is decisive for the analysis. GMK cells were seemed in microtiter plates and preincubated at 5% $CO_2$, 37° C. and with a humidity of 95% in the incubator during 48 h for producing a cell lawn (Schmidtke M et al.: *J Virol Meth,* 2001, 95(1-2), 133-143). Then, the medium was removed and the substances were deposited in different concentrations (100 μl/well/concentration, dilution factor 2) in the culture medium. 100 μl of the medium was used for each of the control value determinations (six untreated cell controls). 72 h after the substance application and incubation, the cells were dyed with crystalviolet/methanol. After the extraction of the dye, the optical density (OD) of the individual cavities were measured in a plate photometer of the Dynatech company (550/630 nm) and compared with the mean value of the cell controls. The mean value of the controls was assumed to be 100 %. By means of the mean dose effect curves the 50% cytotoxic concentrations ($CC_{50}$) were measured by applying the linear interpolation method.

| Examples | 50% cytotoxic concentration (µg/ml) in | |
|---|---|---|
| | HeLa cells | GMK cells |
| 1 | 39.6 | >50 |
| 2 | 45.7 | >50 |
| 3 | 27.7 | not examined |
| 4 | >50 | >50 |
| 5 | 8.5 | 42.9 |
| 6 | 44.3 | >50 |

2.2 Antiviral Effect of the Compounds of the Just Described Examples 1 through 6 in the Cell Culture:

Cytopathic effect (cpE)-inhibition test with the international reference strain coxsackievirus B3 Nancy (CVB3 Nancy), human rhinovirus 2 and 8 (HRV2 and HRV14) in HeLa cells The replication of the viruses used in the test leads to the complete destruction of the host cells, a strong cytophatic effect (cpE). By adding antiviral agents (100 µl/well/concentration, dilution factor 2) the virus-induced cpE can be specifically inhibited (Schmidtke M. et al.: *J Virol Meth*, 2001, 95(1-2), 133-143). In the test, untreated and substance-treated compact cell lawns were infected with a virus dose that leads to a complete cpE in the untreated virus controls 24 h (CVB3 Nancy) or 72 h (HRV2 and HRV8) after the infection. At this point in time, the still adherent cells were fixed and dyed with a crystal-violet/formalin solution. The inhibition of the virus-induced cpE was quantified photometrically in a Dynatach plate reader after dye elution. The antiviral effect was calculated by comparing the optical densities of the substance-treated and untreated, virus-infected cells with the mean optical density of the cell controls that was assumed to be 100%. By means of the mean dose effect curves the 50% inhibition concentration was determined. Pleconaril was used as a control substance. The results achieved with the example substances are shown in the following table.

| Examples | 50% inhibition concentration (µg/ml) | | |
|---|---|---|---|
| | CVB3 Nancy | HRV2 | HRV8 |
| Pleconaril | ineffective | 0.01 | 1.3 |
| 1 | 0.002 | ineffective | ineffective |
| 2 | 0.001 | 4.1 | 4.6 |
| 3 | 0.02 | 1.1 | 1.0 |
| 4 | 0.08 | 1.8 | 2.2 |
| 5 | 0.04 | 0.7 | 1.0 |
| 6 | 0.03 | 0.9 | 2.0 |

Plaque reduction test (PRT) with the substance of example 1 and coxsackievirus B1, B2, B4, B5, B6 (CVB1, CVB2, CVB4, CVB5, CVB6)

For performing the test, 2-3-days-old compact HeLa cell lawns were infected in 12-well-tissue culture plates with 50-80 plaque-forming units (PFU) (Schmidtke M et al.: *J Virol Meth*, 2001, 95(1-2), 133-143). Two non-infected cavities of the plate were used as cell controls (CC). After a virus adsorption at 37° C. during one hour the virus-containing supernatant was soaked off. The infected cells were covered with a test medium containing 0.4% agar without (virus controls) or with substance in non-zytotoxic concentrations (dilution factor 2, double determination per concentration) and incubated at 37° C. during 48 h. After the fixation and dyeing of the plates with crystal-violet formalin, the agar was removed and rinsed in flowing water. The number of the virus-induced plaques was counted via a light box and afterwards the proportional substance-induced plaque reduction was calculated. Three identical test approaches were performed and the concentration that leads to a 50% plaque reduction ($IC_{50}$) was measured by using the calculated mean dose-effect-curve. The results achieved with the substance of example 1 are shown in the following table.

| Viruses | 50% zytotoxic concentration in HeLa cells ($CC_{50}$) in µg/ml | 50% inhibition concentration in HeLa cells($IC_{50}$) in µg/ml | Selection index (SI) = $CC_{50}$:$IC_{50}$ |
|---|---|---|---|
| CVB1 | 39.6 | 12.7 | 3.1 |
| CVB2 | 39.6 | 0.3 | 132 |
| CVB4 | 39.6 | 7.1 | 5.6 |
| CVB5 | 39.6 | 2.8 | 14.1 |
| CVB6 | 39.6 | 2.6 | 15.3 |

2.3 Acute and Subacute Toxicity of the Compounds of the Examples 2 and 4 in the Mouse The acute toxicity of the substances of the examples 2 and 4 were determined in mice which were 4-5 weeks old (without strain designation). 1-2 drops TWIN-80 were added to a 1% aqueous carboxymethyl cellulose solution and this mixture was used to produce a substance suspension. 1500, 2000, 2500, 3000, 4000 or 5000 mg/kg of the substances of the examples 2 and 4 were administered orally to 5 mice, each amount once. On the following three days, the general state of health of the mice, the changes in their weight, their rectal temperatures and their survival rate were determined.

All animals survived up to a substance concentration of 3.000 mg/kg, if the substances of the examples 2 and 4 were administered once (see following table). Neither the general state of health nor the rectal temperature nor the body weight was influenced.

The 50% lethal dose of the two substances was about 3500 mg/kg (calculation according to Kärber in Mayer et al. Virologische Arbeitsmethoden. (Virological working methods) Gustav-Fischer-Verlag, Jena, 1973). After the application of the 5000 mg/kg dose the animals died within 3 to 5 h.

| Concentration (mg/kg) | Number of dead/surviving mice | |
|---|---|---|
| | Example 2 | Example 4 |
| 1500 | 0/5 | 0/5 |
| 2000 | 0/5 | 0/5 |
| 2500 | 0/5 | 0/5 |
| 3000 | 0/5 | 0/5 |
| 4000 | 3/5 | 4/5 |
| 5000 | 5/5 | 5/5 |

On the basis of these results, the substances of the examples 2 and 4 can be considered very tolerable after administering them orally once.

The subacute toxicity of the same substances (examples 2 and 4) was determined in mice which were 4 weeks old (without strain designation). 1-2 drops TWIN80 were added to a 1% aqueous carboxymethyl cellulose solution and this mixture was used to produce substance suspensions. 100 mg/kg of the substances of the examples 2 and 4 were administered perorally to each of 7 mice once during 5 days. The mice were observed over a period of 10 days. Every day, the general state of health, the body weight changes, the changes in the rectal temperature and the survival rate were determined. At the end of the test, morphological changes of the lien, lung and lever were examined after section.

The substance treatment did not have any influence on the general state of health or the body temperature. The body weight of the treated mice increased in the observation period in the same way like the one of the untreated control animals. None of the animals died.

Thus, the substances of the examples 2 and 4 in a concentration of 100 mg/kg can be considered very tolerable after administering them perorally five times.

The invention claimed is:

1. 4-amino-3-arylamino-6-arylpyrazolo[3,4-d]pyrimidine derivatives, characterized by a compound of the general formula I

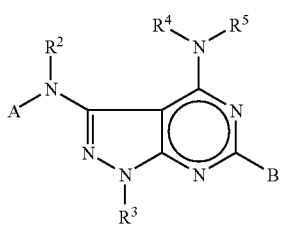

and
pharmaceutically acceptable salts thereof,
wherein:
the groups A and B are phenyl, and optionally and independently of each other, one of the hydrogen atoms on the phenyl groups A and B is substituted with a $R^1$ group,
$R^1$ is fluoro, chloro, bromo, methyl, n-butyl, t-butyl, $OCF_3$, methoxy, ethoxy, O-n-butyl, difluoromethyl or trifluoromethyl,
$R^2$ is H, $R^3$ is H, and $R^4$ and $R^5$ are H.

2. 4-amino-3-arylamino-6-arylpyrazolo[3,4-d]pyrimidine derivatives according to claim 1, comprising a 4-amino-6-phenyl-3-($R^1$)phenylaminopyrazolo[3,4-d]pyrimidine of the general formula I, and $R^1$ in the groups A and B are, independently of each other, fluoro, chloro, bromo or trifluoromethyl, and pharmaceutically acceptable salts thereof.

3. 4-amino-3-arylamino-6-arylpyrazolo[3,4-d]pyrimidine derivatives according to claim 1, comprising a 1-$R^3$-4-amino-6-phenyl-3-($R^1$)phenyl-aminopyrazolo[3,4-d]pyrimidine of the general formula I, and the $R^1$ group in the groups A and B are, independently of each other fluoro, chloro, bromo or trifluoromethyl, and pharmaceutically acceptable salts thereof.

4. 4-amino-3-arylamino-6-arylpyrazolo[3,4-d]pyrimidine derivatives according to claim 1, selected from the group consisting of:
4-amino-6-phenyl-3-($R^1$)phenylaminopyrazolo [3,4-d]pyrimidine, 4-amino-6-($R^1$)phenyl-3-phenylaminopyrazolo[3,4-d]pyrimidine, and pharmaceutically acceptable salts thereof.

5. 4-amino-3-arylamino-6-arylpyrazolo[3,4-d]pyrimidine derivatives according to claim 1, comprising 6-phenylaminopyrazolo[3,4-d]pyrimidines and the $R^1$ group in the groups A and B are, independently of each other, fluoro, chloro, or bromo, and pharmaceutically acceptable salts thereof.

6. 4-amino-3-arylamino-6-arylpyrazolo[3,4-d]pyrimidine derivatives according to claim 1, selected from the group consisting of:
4-amino-3-(3-chlorophenyl)amino-6-phenylpyrazolo[3,4-d]pyrimidine,
4-amino-3-(3-methoxyphenyl)amino-6-phenylpyrazolo [3,4-d]pyrimidine,
4-amino-3-(4-fluorophenyl)amino-6-phenylpyrazolo[3,4-d]pyrimidine,
4-amino-3-(4-fluorophenyl)amino-6-(4-chlorophenyl) pyrazolo[3,4-d]pyrimidine,
4-amino-3-(4-chlorophenyl)amino-6-phenylpyrazolo[3,4-d]pyrimidine,
4-amino-3-phenylamino-6-phenylpyrazolo[3,4-d]pyrimidine,
4-amino-3-(3-fluorophenyl)amino-6-phenylpyrazolo[3,4-d]pyrimidine,
4-amino-3-(3-methylphenyl)amino-6-phenylpyrazolo[3,4-d]pyrimidine,
4-amino-3-(4-methylphenyl)amino-6-phenylpyrazolo[3,4-d]pyrimidine,
4-amino-3-(4-bromophenyl)amino-6-phenylpyrazolo[3,4-d]pyrimidine, and pharmaceutically acceptable salts thereof.

7. In a method for producing 4-amino-3-arylamino-6-arylpyrazolo[3,4-d]pyrimidine derivatives of claim 1, a step wherein pyrazol is condensed with an arylamadine in the presence of acid or a salt thereof to produce pyrazolo [3,4-d] pyrimidine.

8. The method of claim 7, wherein the acid comprises ethanoic acid or a salt thereof or trifluor ethanoic acid or a salt thereof.

9. The method of claim 8, wherein the salt is acetate.

10. A method of treating a human or animal infected with a picornavirus selected from the group of coxsackie viruses and rhinoviruses, comprising administering to the human or animal a biologic agent or pharmaceutical composition comprising a compound according to any of claims 1 to 6.

* * * * *